US009604772B2

(12) United States Patent
Friedrich et al.

(10) Patent No.: US 9,604,772 B2
(45) Date of Patent: Mar. 28, 2017

(54) CONTAINER FOR RADIOACTIVE INVENTORY AND METHOD OF MAKING SAME

(71) Applicant: GNS Gesellschaft für Nuklear-Service mbH, Essen (DE)

(72) Inventors: Peter Friedrich, Herten (DE); Falk Boehme, Essen (DE); Roland Hueggenberg, Bochum (DE); Joern Becker, Essen (DE)

(73) Assignee: GNS GESELLSCHAFT FUER NUKLEAR-SERVICE mbH, Essen (DE)

( * ) Notice: Subject to any disclaimer, the term of this patent is extended or adjusted under 35 U.S.C. 154(b) by 0 days.

(21) Appl. No.: 15/051,906

(22) Filed: Feb. 24, 2016

(65) Prior Publication Data

US 2016/0251138 A1 Sep. 1, 2016

(30) Foreign Application Priority Data

Feb. 26, 2015 (EP) .................................... 15156784

(51) Int. Cl.

| | |
|---|---|
| ***A61L 2/08*** | (2006.01) |
| ***G21F 9/22*** | (2006.01) |
| ***B65D 81/02*** | (2006.01) |
| ***G21F 5/08*** | (2006.01) |
| ***G21F 5/12*** | (2006.01) |
| ***B22D 25/00*** | (2006.01) |
| ***B65D 85/00*** | (2006.01) |

(52) U.S. Cl.
CPC ......... *B65D 81/022* (2013.01); *B22D 25/005* (2013.01); *B65D 85/70* (2013.01); *G21F 5/08* (2013.01); *G21F 5/12* (2013.01)

(58) Field of Classification Search
CPC . A61L 2/08; A61L 2/081; A61L 2/087; G21F 1/00; G21F 1/02; G21F 1/04; G21F 1/06; G21F 1/08; G21F 1/085; G21F 1/10; G21F 5/06; G21F 5/08; G21F 7/015
USPC ..... 250/505.1, 515.1, 506.1, 453.11, 454.11, 250/455.11, 516.1, 518.1, 519.1
See application file for complete search history.

(56) References Cited

U.S. PATENT DOCUMENTS

| | | | |
|---|---|---|---|
| 5,381,751 A * | 1/1995 | Richards ................. | B09B 1/002 114/264 |
| 7,250,119 B2 * | 7/2007 | Sayala ...................... | G21F 1/00 250/506.1 |
| 9,281,090 B2 * | 3/2016 | Leleu ...................... | G21F 7/015 |
| 2016/0251138 A1 * | 9/2016 | Friedrich ............. | B22D 25/005 |

* cited by examiner

*Primary Examiner* — David A Vanore
(74) *Attorney, Agent, or Firm* — Andrew Wilford

(57) ABSTRACT

A container for radioactive inventory has an end wall, a side wall, and a container lid that form a closed chamber for the radioactive inventory. A plastically deformable layer is provided between the container lid and the inventory and is of such a composition that, in the event of an impact of the inventory against the container lid, at least a majority of the impact forces are uniformly distributable over at least a majority of a surface of the plastically deformable layer.

18 Claims, 1 Drawing Sheet

CONTAINER FOR RADIOACTIVE INVENTORY AND METHOD OF MAKING SAME

FIELD OF THE INVENTION

The present invention relates to a container for radioactive inventory. More particularly this invention concerns such a container and a method of making it.

BACKGROUND OF THE INVENTION

A standard container for nuclear inventory has an end wall, a side wall, and a lid. The container forms a closed chamber for the radioactive inventory.

In such containers the connection of the container lid to the side wall forms under extreme circumstances a relative weak point because the connection is often reversible. For example, screws are understood as reversible connections. Since such the containers are characterized by a very long life, the containers have to be configured for a number of extreme situations. Herein included are, for example, extreme impact situations such as falls from a height of several meters. In the case of such falls, the potential energy of the container is converted into deformation energy, and, based on the solid construction of the container walls, the greatest force is exerted on the screws, in particular when the container lands in a so-called "lid flat fall" with the lid down, that is on its lid. If the yield point of the screws is exceeded, the screws are plastically deformed. In an extreme case, the plastic deformation can lead to a leakage of the container.

From practice is it further known to provide containers holding fuel elements with plastically deformable shock absorbers within the container. These shock absorbers are cylindrically tubular and made of aluminum. In the case of a fall through several meters on the horizontal lid, the fuel elements crash onto the hollow cylindrical shock absorbers, as a result of which the shock absorbers are plastically deformed in an accordion-like manner. This plastic deformation of the shock absorbers dissipates a considerable portion of the potential energy so that the stresses in the screws are reduced at least to the extent that no plastic deformations of the screws results. However, the hollow cylindrical shock absorbers from the prior art known from the practice are attached via further screws to the inner face of the lid. Consequently, threaded holes are required on the inner face of the lid, as a result of which the lid loses stability. Moreover, the manufacture of the hollow cylindrical shock absorbers as well as their attachment on the inner face of the lid require a certain effort. After all, the inventory in form of the fuel elements has to be guided to the shock absorbers by guide heads to ensure that the inventory does not slide past the shock absorbers and, in this way, crash in an uncushioned manner onto the lid.

OBJECTS OF THE INVENTION

It is therefore an object of the present invention to provide an improved container for radioactive inventory and method of making same.

Another object is the provision of such an improved container for radioactive inventory and method of making same that overcomes the above-given disadvantages, in particular that avoids the disadvantages described above, in particularly by being of simpler construction with respect to the manufacture and installation of the shock absorbers.

SUMMARY OF THE INVENTION

A container for radioactive inventory has according to the invention an end wall, a side wall, and a container lid that form a closed chamber for the radioactive inventory. A plastically deformable layer between the container lid and the inventory is plastically deformable such that, in the event of an impact of the inventory against the container lid, at least a majority of the impact forces are uniformly distributable over at least a majority of a surface of the plastically deformable layer.

For example, pellets, sheared steel scrap and solid elements are considered as radioactive inventory. The radioactive inventory may also be at least one barrel or a plurality of barrels. In addition to the radioactive inventory, water can also be in the container. For this reason, the container for radioactive inventory is suited to isolate inventory from the surroundings in a fluid-proof manner. Moreover, the container is suited for a sufficient radioactive shielding via thick metal-like container walls. The end wall and/or the lid is/are reversibly or irreversibly connected to the side wall. Screws, for example, represent reversible connections. Welded connections, for example, represent irreversible connections. Preferably, the end wall is irreversibly connected to the side wall. It is advantageous that the lid is reversibly connected to the side wall.

Most of all solid bodies are, to a certain degree, elastically and also plastically deformable. The expression "plastically deformable" in terms of the present invention, for this reason, means that the body is primarily plastically deformable. In particular hollow structures of most different kinds made from most different materials are included therein. The empty chambers can have regular, geometric shapes such as honeycombs. The empty chambers can, however, also be designed in as bubbles so that the plastically deformable element then is a solidified foam.

The term "layer" can reference a completely flat element but also a plurality of elements distributed over an area. For this reason, the plastically deformable layer can assume different shapes. The plastically deformable layer can, for example, be a circle or a square or comprise a plurality of rings concentric to one another. The layer can be a checkerboard or a plurality of points. A combination of different area shapes is also possible.

In order of being able to uniformly distribute the impact forces, the layer has to be designed in a continuous manner or the individual elements of the layer have to be designed approximately equal in strength. This ensures that the forces of impact of the inventory is not transferred too strongly at some points to one or a plurality of protruding layer regions. In particular, solid bodies are not allowed to be between the plastically deformable layer regions or surrounding the layer regions in such a manner that the impact forces are transferred in total or in part to the lid and, in this way, that the plastically deformable layer is bypassed. In particular, the plastically deformable layer is configured such that, for example, a plate is placed onto the plastically deformable layer so that it can uniformly distribute the impact forces of at least a majority of the inventory to at least a majority of the surface. The term "majority" means preferably 50%, more preferably 75% and particularly preferably 100%. Such a configuration of the plastically deformable layer ensures that the kinetic energy of the impact can be distributed over a particularly large area, as a result of which the plastically deformable layer can be designed considerably thinner.

It is within the scope of the present invention that the plastically deformable layer has a specific energy absorption of 5 to 50 J/cm$^3$, preferably of 15 to 40 and, particularly preferably, of 20 to 30 J/cm$^3$ in the vertical direction. The specific energy absorption is a substantially volume-independent measurement of the plastically deformable layer. The lower the specific energy absorption, the thicker the plastically deformable layer has to be so that a respectively high amount of kinetic energy can be absorbed by the plastically deformable layer. However, the specific energy absorption cannot be arbitrarily high because otherwise the stresses in the screws can become so great that plastic deformations also occur in the screws. The indicated ranges of the specific energy absorption are largely independent from the configuration of the container and of the inventory so that they represent a basic statement about the nature of the plastically deformable layer. The specific energy absorption can particularly be adjusted via average empty chamber volumes or via the respective material. The higher the empty chamber volumes, the harder the material system for a specified, desired specific energy absorption has to be, and vice versa.

It is within the scope of the present invention that the plastically deformable layer is isotropic. In this instance, the term "isotropic" means that the plastically deformable layer is plastically deformable in an approximately equal manner in all spatial directions. An example for isotropic plastically deformable materials is solidified foams. In contrast, empty chamber structures having geometrically regular dimensions such as honeycomb chambers are, as a rule, not isotropically deformable.

Preferably, the plastically deformable layer is a metal foam. The metal foam advantageously has closed cells. It is within the scope of the present invention that the plastically deformable layer is aluminum and, according to a particularly preferable embodiment, is made out of aluminum foam or substantially out of aluminum foam. Advantageously, the aluminum foam is made out of at least 90 wt %, preferably out of at least 95 wt % and particularly preferably out of 97 wt % aluminum. Preferably, the plastically deformable layer is an Al—Mg—Si alloy. More preferably, the plastically deformable layer has remnants of a foaming agent. Very preferably, the plastically deformable layer has remnants of titanium.

It is preferred that the plastically deformable layer is encapsulated and/or coated. Preferably, the plastically deformable layer is encapsulated and closed cell. The encapsulation ensures that, in the case of a closed cell metal foam, micro cracks are counteracted and, in this way, the plastically deformable layer is kept water-tight. The water-tightness prevents oxidation of the metal foam, as a result of which the metal foam has consistently good deformation properties over a long period of time.

It is within the scope of the present invention that the plastically deformable layer has a thickness of 30 to 200 mm, preferably 40 to 150 mm and particularly preferably 50 to 100 mm. The density of the plastically deformable layer is preferably 0.1 to 2 g/cm$^3$, furthermore preferably 0.2 to 1.3 g/cm$^3$ and particularly preferably 0.5 to 0.9 g/cm$^3$. Preferably the plastically deformable layer is configured in a circular and/or annular manner.

Preferably, the plastically deformable layer is attached directly to the inner face of the container lid. The term "directly" means that, in particular, nothing encloses the plastically deformable layer or is between the plastically deformable layer and the lid.

According to one embodiment, the plastically deformable layer is unitarily bonded to the lid. Preferably, the plastically deformable layer is adhesively bonded or welded and, particularly preferably, the plastically deformable layer has, during foaming, been molded to the lid. According to a further embodiment, the plastically deformable layer is attached to the lid by screws.

Another preferred embodiment of the present invention is characterized by the fact that a lead shielding lid is interposed between the lid and the plastically deformable layer. In this instance, it is within the scope of the present invention that the lead shielding lid is attached to the container lid by a flat holding element, in particular, by a plate. In this case, the flat holding element or plate is between the lead shielding lid and the plastically deformable layer and, for this reason, the assembly of the lead shielding lid and the flat holding element or holding plate is positioned between the lid and the plastically deformable layer. In this embodiment, the plastically deformable layer is advantageously attached directly to the lead shielding lid or to the flat holding element or to the holding plate. In this instance, the plastically deformable layer can be attached by screws. Alternatively or additionally, the plastically deformable layer can also be unitarily connected to the lead shielding lid or to the flat holding element. In this way, the plastically deformable layer can be adhesively bonded or welded onto the lead shielding lid or onto the flat holding element and, according to one embodiment, the plastically deformable layer can, during foaming, be molded to the lead shielding lid or to the flat holding element. According to a recommended embodiment, attaching the plastically deformable layer "directly" to the lead shielding lid or the flat holding element means in particular that nothing encloses the plastically deformable layer and that nothing comes between the plastically deformable layer and the lead shielding lid or the flat holding element.

In general, it is also within the scope of the present invention that the plastically deformable layer is enclosed by a casing, in particular, by a water-tight casing. Furthermore, it is also within the scope of the present invention that the plastically deformable layer has been foamed in an envelope, in particular, in a water-tight envelope.

According to a recommended embodiment of the present invention, a lead shield is also provided on the container inner face of the side wall and of the end wall. Then, it is within the scope of the present invention that the total interior of the container is encapsulated by a lead shield. The thickness of the lead shield is preferably between 20 and 40 mm.

Advantageously, the side walls of the plastically deformable layer enclose a fluid at least in areas. The term "fluid" refers to liquid and gas and, in particular, air or water. Advantageously, the side walls of the plastically deformable layer are spaced from the inner face of the side wall or from the inner face of the lead shield at the side wall. Preferably, the spacing between at least one side wall of the plastically deformable layer and the inner face of the side wall or the inner face of the lead shied is 0 to 100 mm, in particular 10 to 90 mm and preferably 20 to 90 mm.

According to a preferred embodiment, a load distributor is between the plastically deformable layer and the inventory. Advantageously, the load distributor is a load distribution plate. According to another embodiment, the load distributor is a basket lid enclosing the radioactive inventory. According to another embodiment, the radioactive inventory itself is provided with a surface facing the lid and parallel to the lid. It is within the scope of the present invention that the surface of the radioactive inventory facing the lid and parallel to the lid is formed by small parts of elements, for example, pellets.

According to a particularly preferable embodiment, the load distributor comprises a load distribution plate. Advantageously, the load distribution place is made out of fine-grain construction steel. It is preferred that the thickness of the load distribution plate is 5 to 40 mm, furthermore preferably 10 to 30 mm and particularly preferably 15 to 25 mm. The 0.2% yield point of the load distribution plate is advantageously 600 to 1600 MPa, furthermore advantageously 800 to 1400 MPa and particularly advantageously 1000 to 1200 MPa. These measures prevent in particular a punching through of the load distributor.

Advantageously, the lid is attached to the side wall via reversible fasteners. Preferably, the reversible fasteners are screws. The screws of the screw connections have external threads of advantageously 24 to 64 mm, preferably 30 to 56 mm and particularly preferably of 36 to 48 mm.

It is within the scope of the present invention that the side wall has a thickness of 100 to 350 mm, preferably of 120 to 250 mm and particularly preferably of 140 to 180 mm. The interior height of the container is advantageously from 0.5 to 10 m and preferably from 0.5 to 5 m. According to a particularly preferred embodiment of the present invention, the interior height of the container is from 0.6 to 2 m, particularly from 0.7 to 1.5 m. Preferably, the side and end walls are cast as one piece. It is preferred that the side wall and the end wall and also the lid are of cast iron. The cast iron is preferably attributed to Quality GGG 40.

In order to solve this problem, the present invention further teaches a method of making a container for radioactive inventory, in particular of making a container according to the present invention, the container having an end wall, a side wall, and a lid and enclosing an interior space for the radioactive inventory, at least one plastically deformable layer being between the container lid and the inventory, and the plastically deformable layer being configured in such a manner that the impact forces of at least a majority of the inventory are uniformly distributable over at least a majority of the surface of the plastically deformable layer. As described above, the container, according to a particularly preferable embodiment of the present invention can also have a lead shield on its inner face, the lead shield advantageously on the inner face of the lid and/or on the inner face of the side wall and/or on the inner face of the end wall.

It is within the scope of the present invention that the plastically deformable layer is made out of a metal foam or substantially is made out of a metal foam. According to a particularly recommended embodiment, the plastically deformable layer is made out of an aluminum foam or is substantially made out of an aluminum foam. Preferably, the metal foam is foamed by a foaming agent. Preferably, the foaming agent is titanium hydride. According to a particularly preferable embodiment, the metal foam is unitarily bonded by foaming to the lid or to the lead shielding lid or to the flat holding element on the lead shielding lid. Preferably, the foaming also unitarily connects the metal foam to a load distributor. Categorically, attaching or connecting the plastically deformable layer or the metal foam can also occur via screw connections.

The discoveries of the present invention are that the plastically deformable layer results in considerably simplifying the container. A further consequence is that the shock absorber in the form of the plastically deformable layer has a smaller height, as a result of which more usable space is available. In particular, employing the metal foam enables economic manufacture of the shock absorber that almost entirely can absorb the kinetic energy. By encapsulating or coating, the metal foams can be designed having a particularly long service life. Load distributors enable a surface distribution of the impact forces and prevent punching through the plastically deformable layer. As a result, the plastically deformable layer can be designed in an even thinner manner without risk.

BRIEF DESCRIPTION OF THE DRAWING

The above and other objects, features, and advantages will become more readily apparent from the following description, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing.

SPECIFIC DESCRIPTION OF THE INVENTION

Figure 1:
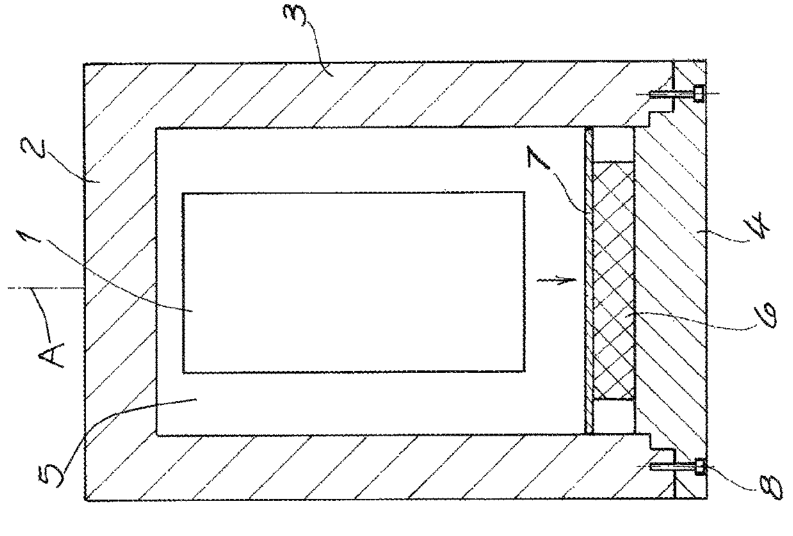
FIG. 1 is a schematic cross-section of the container according to the present invention.

FIG. 1 shows a container according to the present invention having an end wall 2, a tubularly cylindrical side wall 3 centered on a normally vertical axis A, and a lid 4 here shown closing the open bottom end of the side wall 2. The container is hollow and cylindrical and forms a closed chamber 5 in which an only schematically represented radioactive inventory 1 is located. The lid 4 is connected via screw connections 8 in the form of 24 M36 screws to the side wall 3. The container walls 2, 3, and 4 are made out of cast iron of quality GGG 40. The side wall 3 has a thickness of 160 mm; in contrast, the end wall 2 and the lid 4 each have a thickness of 180 mm. The hollow cylindrical interior space 5 has a height of 1140 mm and a diameter of 740 mm. The side wall 3 and 3 end wall are unitarily cast with each other.

The container is shown upside down to illustrate a lid flat fall. At the time of lid-first impact onto a solid base, the inventory 1 strikes the lid 4 with a time delay so that significant forces act upon the lid 4.

According to the invention a plastically deformable layer 6 is attached to the inner face of the lid 4 in the form of a block of aluminum foam here formed as a cylindrical plinth of a diameter smaller than the inside diameter of the side wall 3. The aluminum foam has been foamed by use of the foaming agent titanium hydride. The thermal energy expended during foaming results in a liquefying of the aluminum and, when the aluminum foam cools, it bonds to the lid 4. During foaming, the aluminum foam of the deformable plastic layer 6 is limited in the upward direction by a load distributor 7 in the form of a load distribution plate of cylindrical shape and a diameter equal substantially to the inside diameter of the side wall 3. The load distributor 7 is bonded to the aluminum foam just like the lid 4.

The aluminum foam is plastically deformable to an approximately equal extent in all spatial directions and, for this reason, is isotropic. The aluminum foam is closed cell and is encapsulated for the purposes of water-tightness. The aluminum foam has a density of 0.7 g/cm$^3$, a thickness of 70 mm and a diameter of 585 mm when circular. The 0.2% yield point of the load distributor 7 in the form of a circular load distribution plate made from fine-grain construction steel is 1100 MPa. The thickness of the load distributor 7 is 20 mm.

Figure 2:
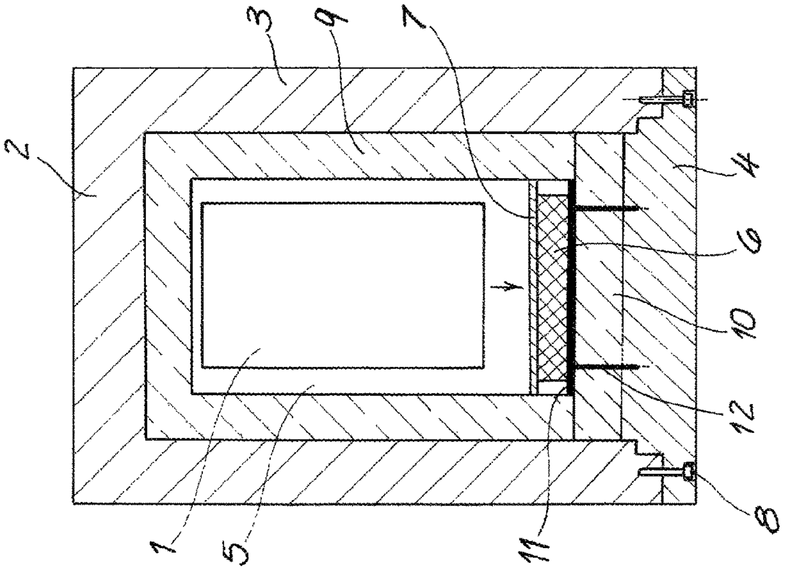
FIG. 2 is a schematic view of another embodiment of the container according to FIG. 1.

FIG. 2 illustrates a different embodiment of the container according to the present invention. The same components of FIG. 1 are here provided with the same reference characters. Compared to the embodiment of FIG. 1, the container according to FIG. 2 has an additional inner lead shield 9 entirely lining and delaminating the chamber 5. Here, this lead shield 9 is inside the container at the end wall 2 as well as also on the side wall 3 and a lead shielding lid 10 is provided on the lid 4. In the embodiment according to FIG. 2, the lead shielding lid 10 is kept and fixed to the lid 4 by a holding plate 11 itself fixed to the lid 4 by screws 12 that extend through the lead shield lid 10. Thus, advantageously and in the illustrated embodiment according to FIG. 2, the assembly of the lead shielding lid 10 and holding plate 11 is interposed between the deformable plastic layer 6 of aluminum foam and the lid 4.

Figure 3:
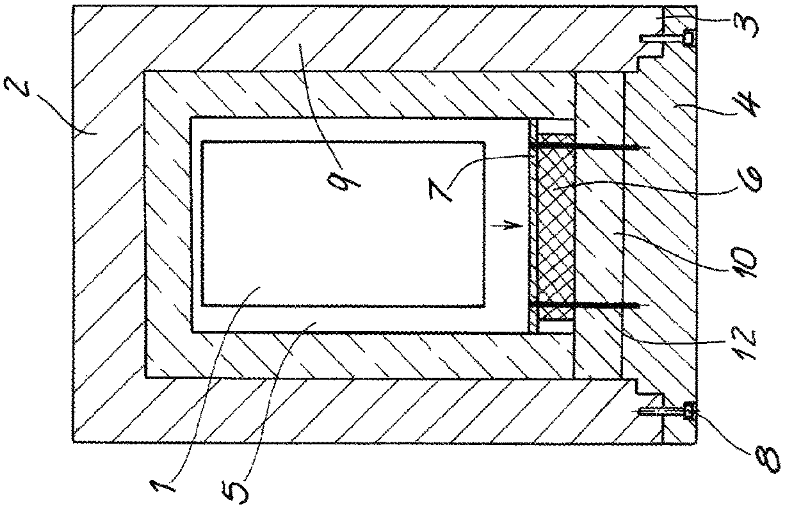
FIG. 3 is a schematic view of yet another embodiment of the container according to FIG. 1.

In the embodiment according to FIG. 3, the holding plate 11 is omitted. Instead, the lead shielding lid 10 is fixed to the lid 4 by the load distributor 7 or by the load distribution plate. The screws 12 in FIG. 3 reach here from the load distributor 7 or the load distribution plate 7 through the force-distribution layer 5 and the lead shield lid 10 into the lid 4.

We claim:

1. A container for radioactive inventory comprising:
- an end wall, a side wall, and a container lid that form a closed chamber for the radioactive inventory;
- a plastically deformable layer between the container lid and the inventory and of such composition that, in the event of an impact of the inventory against the container lid, at least a majority of the impact forces are uniformly distributable over at least a majority of a surface of the plastically deformable layer.

2. The container defined in claim 1, wherein the plastically deformable layer has a specific energy absorption of 10 to 50 J/cm$^3$ in a vertical direction.

3. The container defined in claim 1, wherein the plastically deformable layer is isotropically deformable.

4. The container defined in claim 1, wherein the plastically deformable layer is a metal foam.

5. The container defined in claim 4, wherein the plastically deformable layer contains aluminum.

6. The container defined in claim 1, wherein the plastically deformable layer is encapsulated or coated.

7. The container defined in claim 1, wherein the plastically deformable layer has a thickness of 30 to 200 mm.

8. The container defined in claim 1, wherein the plastically deformable layer is of circular shape.

9. The container defined in claim 1, wherein the plastically deformable layer is attached directly to an inner face of the container lid.

10. The container defined in claim 9, wherein the plastically deformable layer is bonded unitarily to the inner face of the container lid.

11. The container defined in claim 1, further comprising:
- a lead shield lining the side wall and end wall;
- a shield lid lining the container lid; and
- a flat holding element for the shield lid interposed between the plastically deformable layer and the shield lid, the plastically deformable layer being attached directly to the lead shielding lid or to the flat holding element.

12. The container defined in claim 1, wherein edges of the plastically deformable layer at least in areas border a fluid.

13. The container defined in claim 1, further comprising:
- a load distributor between the plastically deformable layer and the inventory.

14. The container defined in claim 12, wherein the load distributor is a plate.

15. The container defined in claim 1, further comprising:
- a reversible fastener securing the container lid to the side wall.

16. The container defined in claim 1, wherein the side wall has a thickness of 100 to 350 mm.

17. A method of making a container for radioactive inventory comprising the steps of:
- providing an end wall, a side wall, and a lid together forming a closed chamber for the radioactive inventory;
- interposing between the lid and the inventory at least one plastically deformable layer of such composition that impact forces of at least a majority of the inventory are uniformly distributable over at least a majority of a surface of the plastically deformable layer in the event of the container being dropped.

18. The method defined in claim 17, wherein the plastically deformable layer is formed by in situ foaming of aluminum in the container between the container lid and the inventory such that the layer bonds unitarily to the container lid.

* * * * *